United States Patent [19]
Anderson

[11] Patent Number: 5,290,278
[45] Date of Patent: Mar. 1, 1994

[54] METHOD AND APPARATUS FOR APPLYING THERMAL ENERGY TO LUMINAL TISSUE

[75] Inventor: Dallas W. Anderson, The Woodlands, Tex.

[73] Assignee: Proclosure Inc., Winter Park, Fla.

[21] Appl. No.: 972,532

[22] Filed: Nov. 6, 1992

Related U.S. Application Data

[63] Continuation-in-part of Ser. No. 963,585, Oct. 20, 1992, abandoned.

[51] Int. Cl.5 ............................................. A61B 17/36
[52] U.S. Cl. ............................................. 606/15; 606/8
[58] Field of Search .............. 606/2, 3, 7–16; 128/395–398; 607/88, 89

[56] References Cited

U.S. PATENT DOCUMENTS

| | | | |
|---|---|---|---|
| 4,633,870 | 1/1987 | Sauer | 606/16 |
| 4,672,969 | 6/1987 | Dew | 606/8 |
| 4,790,310 | 12/1988 | Ginsburg et al. | 128/398 |
| 4,929,246 | 5/1990 | Sindesky | 606/8 |
| 5,019,075 | 5/1991 | Spears et al. | 606/7 |
| 5,178,617 | 1/1993 | Kuizenga et al. | 606/9 |

*Primary Examiner*—Stephen C. Pellegrino
*Assistant Examiner*—M. Peffley
*Attorney, Agent, or Firm*—Steven C. Stewart

[57] ABSTRACT

A method and apparatus for sealing luminal tissue is disclosed. The apparatus is inserted into the lumen of the organ and positioned adjacent an area on the organ to be sealed. Energy sufficient to heat tissue to form a denatured proteinaceous substance is delivered through the lumen to the apparatus. The apparatus then directs the energy at the area to be sealed.

11 Claims, 3 Drawing Sheets

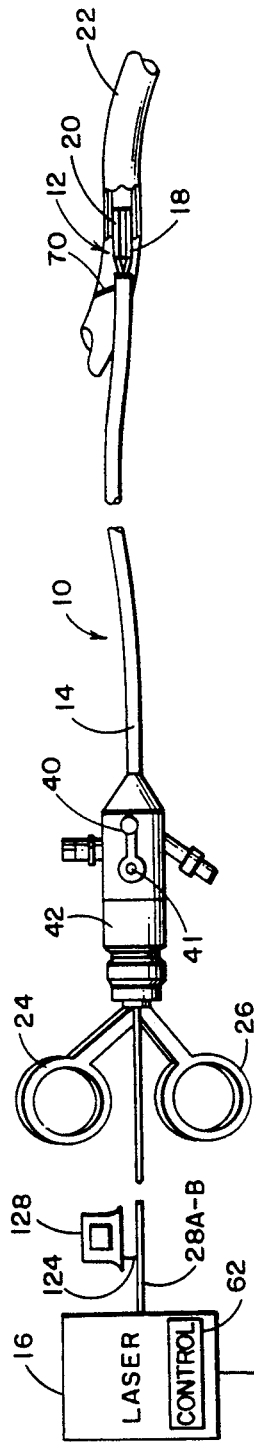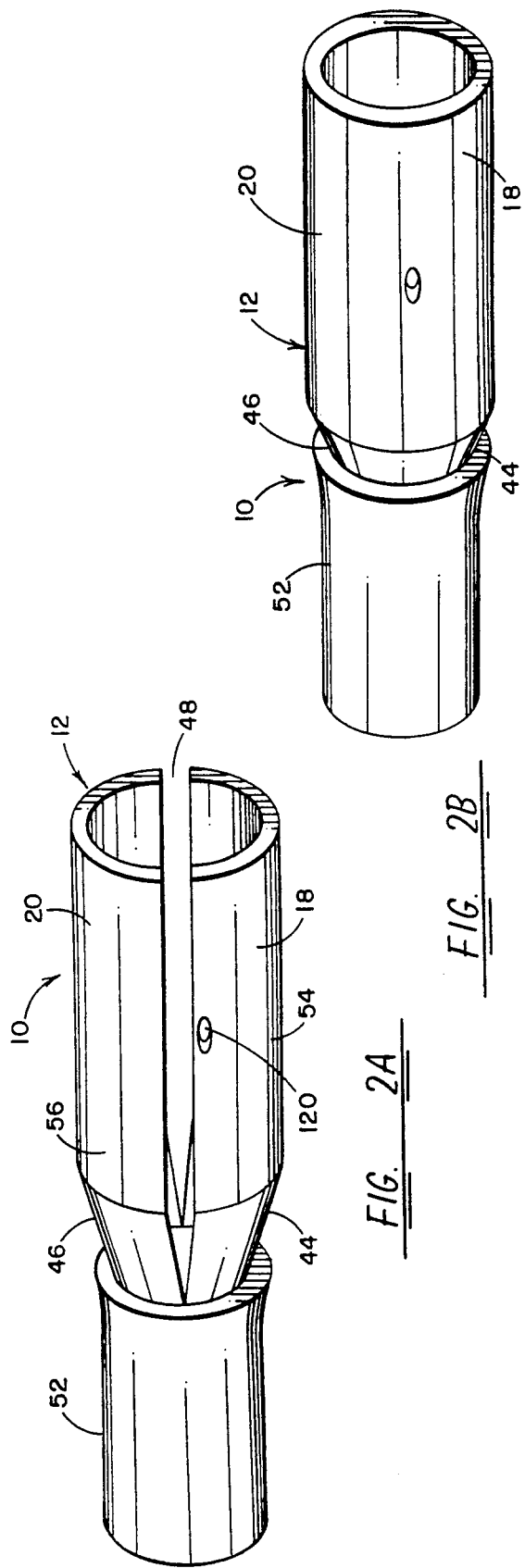
FIG. 1
FIG. 2A
FIG. 2B

METHOD AND APPARATUS FOR APPLYING THERMAL ENERGY TO LUMINAL TISSUE

This is a Continuation-In-Part of application Ser. No. 07/963,585, filed Oct. 20, 1992, now abandoned.

BACKGROUND OF THE INVENTION

This invention relates to a method and apparatus for applying thermal energy to biological luminal tissue whereby tissue is converted to a denatured protein substance to join tightly approximated luminal tissue segments, and, more particularly to a method and apparatus for reconstructing severed tissue, including vessels and ducts by use of a device which is inserted into the tissue to hold edges of the tissue in tight proximity while directing thermal energy onto the tissue to denature the protein substance therein.

Optical energy transformed to thermal energy has been used to convert biological tissue into a denatured proteinaceous substance for facilitating healing and wound closure. This healing technique is referred to generally as laser tissue welding. Examples of such is laser tissue welding methods are described in U.S. Pat. Nos. 4,672,969, 4,854,320, 5,002,051, and 5,140,984. These methods deliver optical energy to tightly approximated tissue in the vicinity of a wound. This application of thermal energy results in the denaturation of tissue protein including collagen, with disruption of the cell walls which allows the intra- and intercellular fluids to mix, additional heat further denatures this protein soup which binds together creating something akin to a "biological glue".

In many prior methods of optical energy wound closure, thermal energy is delivered through an optical fiber to the tissue being reconstructed. Typically, one end of the fiber is connected to a laser that supplies optical energy to the wound site. Another end of the fiber is typically spaced a predetermined distance from the tissue, the distance depending on the tissue type. A foot pedal or hand held device activates and deactivates the laser. The parameters such as intensity and duration of the optical energy are controlled so that substantially all of the tissue being heated is raised to a predetermined non-destructive temperature. The minimum predetermined temperature is one at which tissue is converted to a denatured proteinaceous substance. The maximum predetermined temperature is one at which water in the tissue boils.

Other methods known for healing and wound closure include suturing and stapling. These methods are also used in endo-surgery or minimally invasive surgery in combination with various types of scopes, such as endoscopes, laparoscope, arthroscopes, etc. These scopes along with other medical equipment are inserted by a surgeon through incisions in the patient and then moved to the wound area being repaired. The scope is connected to a monitor so that the surgeon can view the procedure while the surgery is being performed.

Laser tissue welding may be used in minimally invasive and open surgery to repair vessels; however, conducting certain minimally invasive and open operations using laser melding surgery can be unnecessarily tedious as the surgeon welds at successive points along the circumference of the vessel or duct. This welding process is complicated because the distal end of the optical media that directs the energy for the welding must be placed a predetermined distance to the tissue being reconstructed or the area being reconstructed. If the distal end of the media is not at the predetermined distance from the area being sealed or reconstructed, the tissue temperature would be outside the aforementioned predetermined temperature range for proper tissue fusion.

Critical to current tissue welding methods is the necessity to place edges of tissue being repaired in tight approximation. Placing the tissue edges in close or tight proximity allows the denatured tissue constituents to form an intercellular matrix resulting in tissue fusion.

Certain luminal tissue types are very difficult for the surgeon to access with current thermal sealing techniques. Consequently, to thermally seal certain organs and vessels, the surgeon may have to cut or displace other organs that are in the way. This can create complications and can be time consuming.

Another sealing technique such as the one disclosed in U.S. Pat. No. 4,892,098, to Sauer requires that a stent device be placed within the lumen of the tissue being sealed for support at a wound. A circular housing is then placed around the tissue and fed optical energy to seal the wound. The proper placement of this stent device and the set up of the circular housing can be time consuming and result in an inconsistent application of optical energy.

SUMMARY OF THE INVENTION

An object of this invention is to provide an improved method and apparatus for reconstructing organs such as tissue, ducts, or vessels.

Another object of this invention is to provide an apparatus through which laser welding energy passes and is directed at the inside walls of luminal organs that are to be sealed, fused, or ligated.

It is also an object of this invention to place a device in the lumen of an organ to cause the formation of a proteinaceous framework for denatured protein in the vicinity of biological tissue to seal tissue, ducts, and vessels with greater efficiency and less time.

It is also an object of this invention to reconstruct transected vessels, organs, and ducts that have incisions by placing an apparatus into the lumen of the vessel and delivering energy to areas along the incision seam completely circumscribing the lumen while maintaining the integrity of the organ and lumen.

It is further an object of this invention to reconstruct tissue with any energy source, such as an ultrasonic or thermal source, while maintaining at all times proper distance between a media delivering the energy to the tissue itself so that the final temperature of the tissue may be precisely maintained.

These and other objects are accomplished with an apparatus for sealing luminal tissue, or organs. The apparatus has a main portion and a tubular portion having an inner surface and a generally arcuate shaped outer surf ace. A device expands the tubular portion away f rom said main portion to engage a tubular organ. Supplied to the apparatus is a source of energy sufficient to heat tissue to form a denatured proteinaceous substance. The energy &s delivered from the source through the inner surface and out the outer surface, when the tubular portion expands to engage the organ, to heat the tubular organ to a temperature within a nondestructive range bounded by a minimum temperature at which tissue forms a denatured proteinaceous substance and a maximum temperature at which water in the tissue would boil. This device can quickly and easily be fed through a lumen and placed adjacent to the area being sealed. While the tubular organ is being sealed the expansion and pressure on the lumen wall maintains the wound edge in proximity.

In another aspect of the invention, a method for sealing luminal tissue, or organs is provided. The includes the steps of first placing an apparatus into a lumen of the organ. Next, energy is emitted from a source sufficient to heat tissue to form a denatured proteinaceous substance. The energy is delivered from the source to the apparatus in the lumen and onto the inner walls along the incision line to be sealed. The delivered energy is applied with sufficient duration and amplitude to heat the tubular organ to a temperature within a nondestructive range bounded by a minimum temperature at which tissue forms a denatured proteinaceous substance and a maximum temperature at which water in the tissue would boil.

BRIEF DESCRIPTION OF THE DRAWINGS

FIG. 1 is a perspective view of one form of the invention having an expansion assembly connected to one end of the energy source and that is inserted in the lumen of an organ;

FIGS. 2A and 2B are perspective views of the expansion assembly in its expanded and retracted position respectively;

DESCRIPTION OF THE PREFERRED EMBODIMENTS

Figure 3:
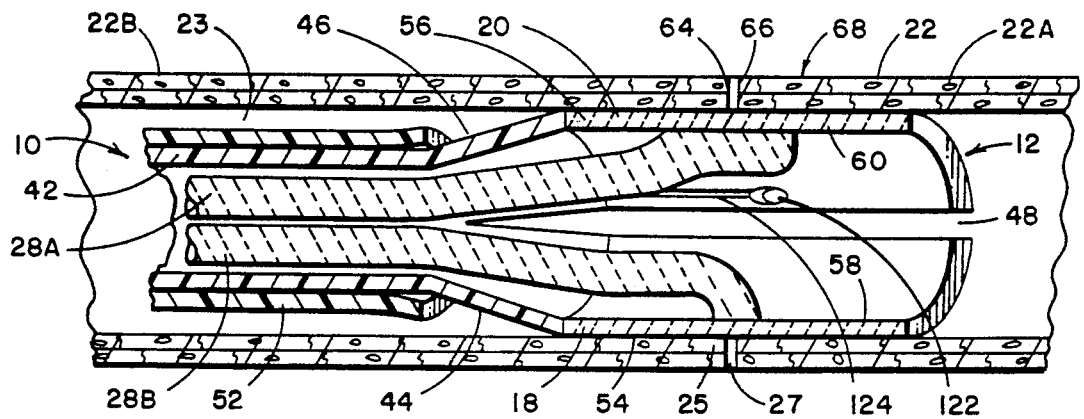
FIG. 3 is a side sectioned view of the expansion assembly shown in FIG. 2A in the expanded position.

Referring to FIGS. 1-3, there is shown an apparatus 10 for tissue welding using an expansion assembly 12 that is fed optical energy through conduit 14 from energy source 16. Assembly 12 includes a first portion 18 and a second portion 20 which engage and disengage with the inner walls of luminal tissue or organ 22 such as a duct or a vessel in response to hand grips 24 and 26 being depressed and released by the user. Optical energy from the energy source 16 is fed through conduit 14 using optical media 28a-28b, such as a fiber optic cable having proximate and distal ends. The proximate end of media 28a-28b is optically connected to the energy source 16. The distal end of fiber optic media 28a-28b terminates in assembly 12 and directs optical energy at the inner walls of organ 22.

Depending on the application, the placement of the media 28 delivering the energy to the tissue can be through various means such as side firing (as shown in media 28a of FIG. 3), end firing (as shown in media 28b of FIG. 3), or other known techniques. Also, the distal end of either media 28a or 28b may be positioned adjacent surfaces 58 and 60, respectively, may be embedded in surfaces 58 and 60, or may direct energy through an aperture in surfaces 58 and 60, or may contact organ 22.

Although shown open, the distal ends of portions 18 and 20 are preferably sealed to prevent fluid from entering assembly 12. Portions 18 and 20 would be sealed with a material that still permits portions 18 and 20 to expand and contract.

Referring to FIGS. 3, organ 22 has a hollow lumen 23 through which fluid flows, surrounded by an outer layer 25 and an inner layer 27 of tissue. The use of the word tubular organs throughout is meant to include all tissue containing a lumen, such as vessels, ducts and arteries. The use of the word lumen is defined as a cavity or the channel within any organ or structure of the body. Assembly 12 engages with the outer layer 27 to seal lesions in tissue, as well as seal closely approximated edges (i.e. a seam) or an incision in a vessel.

Referring to FIGS. 2A-2C, assembly 12 may include one or more feedback sensors (not shown) which detect changes in temperature of organ 22. These feedback sensors would convert detected energy to signals which would be fed to laser source 16. Laser source 16 then responds to the signals by adjusting the energy fed to media 28a-28b to maintain the temperature of the tissue being heated within a predetermined range.

The amount of heat to be absorbed by the organ may be determined by first computing the amount of energy emitted by the source and then subtracting the amount of energy loss through the media to determine the delivered energy. The delivered energy is subtracted from the actual energy detected by the sensor to determine a delta which corresponds to the energy absorbed by the tissue. The energy source can then be controlled as a function of this delta.

Referring to FIG. 1, energy source 16 is activated in response to a foot pedal (not shown) or a trigger assembly 40 being activated. Trigger assembly 40 has a hand trigger that is pivotally connected with pin 41 to member 42. This trigger assembly 40 pivots about pin 41 to enable laser source 16. The parameters in which energy source 16 feeds optical energy through fiber optic media 28a-28b is dependent on the thickness of tissue of the walls of organ 22 to be reconstructed. Examples of these parameters and preferable distances between the ends of fiber optic media 28a-28b and the surface of the inner walls of organ 22 are summarized in the following Table I. These parameters are by no means all exclusive. It is envisioned that other parameters can be used with modifications and it is intended that this table be exemplary of a preferred embodiment only.

TABLE I
LASER PARAMETERS FOR VARIOUS ORGAN TYPES

| Organ Type | Organ Diameter (mm) | Predetermined Distance from media to Organ (with 400μ fiber) (mm) | Spot Size Diameter (mm) | Range of Power (Watts) | Exposure Duration On/Off | Approximate Final Energy Transferred to Organ (J/CM$^2$) |
|---|---|---|---|---|---|---|
| Fallopian Tube | 3 | 1 | .574–646 | .65–.85 | 0.5 sec/0.5 sec | 5.79 |
| Vas Deferens | 3 | 1 | .574–646 | .65–.85 | 0.5 sec/0.5 sec | 5.79 |

Referring to FIGS. 2A–2C and 3, portions 18 and 20 are shown connected to cylindrical throat portion 42 through tapered portions 44 and 46, respectively. Portions 18 and 20 are separated by gap 48 and engage each other along one end of the gap 50. An elongated cylindrical section 52 encircles throat portion 42. A cable or conventional other mechanism (not shown) connects handgrips 24 and 26 to throat portion 42 and cylindrical section 52. The mechanism responds to handgrips 24 and 26 being engaged to force section 52 to slide along tapered portions 44 and 46. Due to the elastic properties of the materials to which portions 18 and 20 are constructed, tubular portions 18 and 20 expand away from and contract toward each other when section 52 slides back and forth along tapered portions 44 and 46,.

Referring to FIG. 3, portions 18 and 20 have respective outside surfaces 54 and 56, and inside surfaces 58 and 60 constructed with a layer of transmissive material shaped of generally arcuate curvature that engages with the inside wall of organ 22. By transmissive material it is intended to mean any material which is substantially transparent to the energy being emitted at the distal ends of media 28a–28b, i.e. the laser frequency.

Figure 4A:
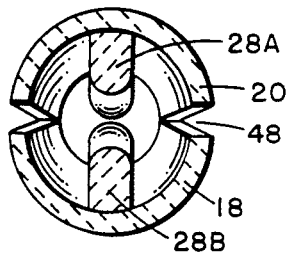
FIGS. 4A and 4B are sectioned views along lines 4A—4A of FIG. A, and FIG. 2B respectively.
Figure 4B:
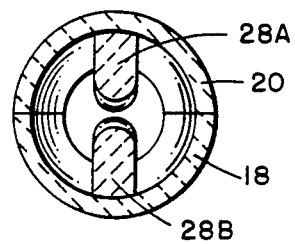
Figure 5:
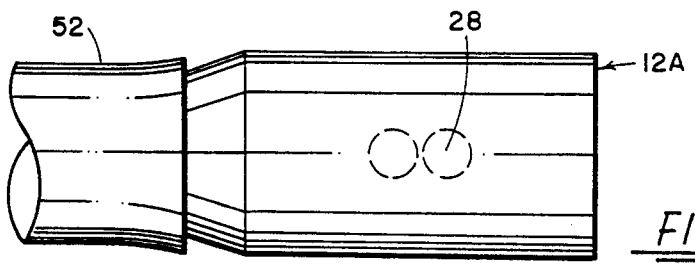
FIG. 5 is a top view of an alternated embodiment of the expansion assembly shown in FIG. 1 for sealing slits in organs.
Figure 6:
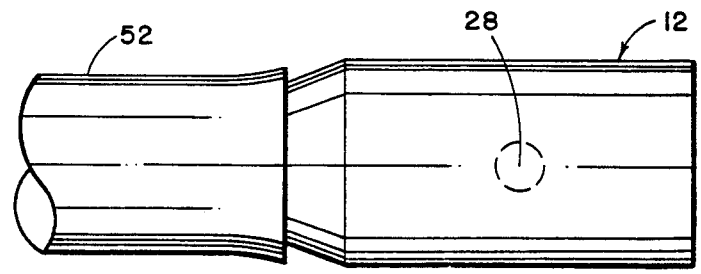
FIG. 6 is a top view of the expansion assembly shown in FIG. 1 for sealing an incision in the tissue.
Figure 7:
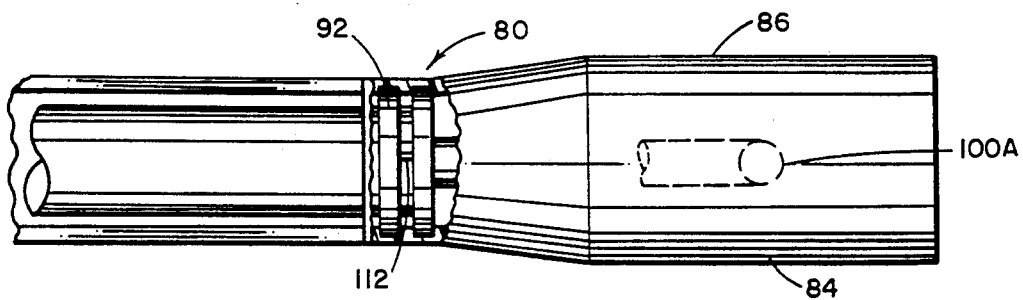
FIG. 7 is a top partially sectioned view of an alternate embodiment of the expansion assembly shown in FIG. 1.
Figure 8:
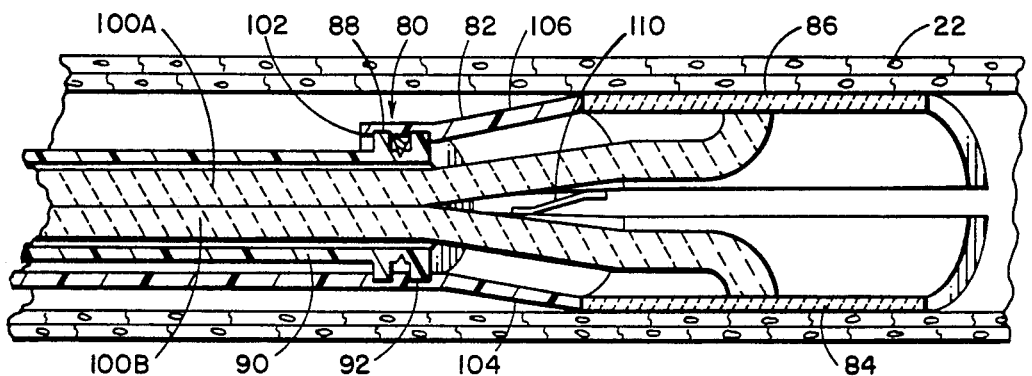
FIG. 8 is a side sectioned view of the expansion assembly shown in FIG. 7.
Figure 9:
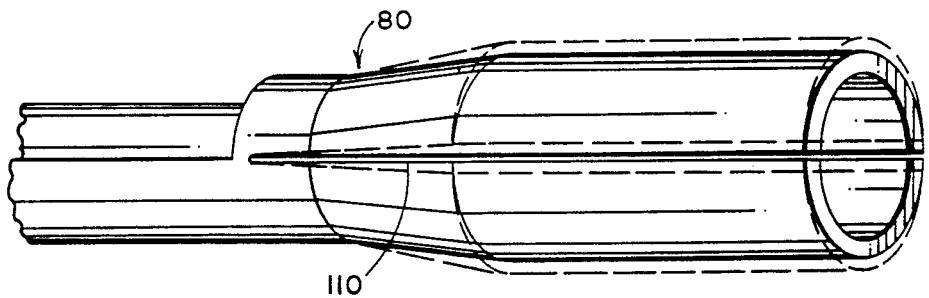
FIG. 9 is a side view of the expansion assembly shown in FIG. 7 having tubular portions that expand away from each other shown in phantom.

Referring to FIGS. 5 and 6, the distal ends of optical media 28 may be positioned at various locations in the transmissive material depending on the application and tissue type. For example, the distal ends of the media would be placed laterally along side each other (FIG. 5) if the apparatus were sealing lengthwise slits in the organ. If the assembly 12 were to seal seams or anastomosis, 68 (See FIG. 3, 4A, 4B, and 6), the distal ends of the media would be placed on opposing inside surfaces of portions 18 and 20.

Referring to FIGS. 3, 4A–4B, the distal end of fiber optic media 28a–28b preferably terminates adjacent the inside surface 58 and 60 of transmissive material. The thickness of the transmissive material is selected to maintain a predetermined distance between the end of fiber optic media 28a–28b and the surface of the inside wall of organ 22. The predetermined distance is selected in accordance with organ 22 type and thickness.

Referring to FIG. 1, energy source 16 contains a control 62 that adjusts the rate at which energy is applied to organ 22 to be within a nondestructive range bounded by a minimum rate at which tissue forms a denatured proteinaceous substance and a maximum rate at which water in the tissue would boil. The rate as used herein is the power and duration of the applied energy. An exemplary control device is described in U.S. Pat. No. 4,854,320 which is hereby incorporated by reference. Preferably the maximum energy rate is selected at a level slightly below that of which shrinkage of the tissue is prevented. Parameters of the rates at which the tissue is heated are previously described herein.

Referring to FIG. 2A and FIG. 3, the curvature of the transmissive material surfaces 54 and 56 are selected to engage the inside walls of organ 22. Expansion assembly 12 is preferably used to seal transected vessel segments 22a and 22b (FIG. 3). To seal the transected vessel, the edges 64 and 66 of the transected vessel segments 22a and 22b are placed in tight proximity to form a seam 68 using conventional means. Next, the expansion assembly 12, with the cylindrical section 52 fully forward and portions 18 and 20 fully contracted as shown in FIGS. 2B, 4B and 6, is fed through a slit 70 in organ 22 to the area of the organ 22 to be sealed. Once the expansion assembly is in proper position, with distal ends of media 28a and 28b aligned on the seam 68 (FIG. 3), cylindrical section 52 is retracted along tapered portions 44 and 46 (See FIG. 2A, 3 and 4A). This retraction allows portions 18 and 20 to expand away from each other and engage the inner walls of organs 22a and 22b. This engagement holds edges 64 and 66 in alignment along seam 68.

Energy source 16 is then activated and energy is delivered through media 28a–28b to seam 68 of organ 22 to form a denatured proteinaceous substance that seals the seam. The amount of energy provided and the duration of the energy is dependent on the tissue type as previously discussed.

Optical energy may be delivered to the inside walls of the organ 22 simultaneously through media 28a and 28b. Alternately, the optical energy may be delivered through each of media 28a and 28b in a sequential manner, i.e. first through media 28a, then media 28b. The distal ends of media 28a–28b are placed in assembly 12 to deliver optical energy to one or more areas that circumscribe organ 22 adjacent the transection. After sealing seam 68, cylindrical section 52 is moved forward to its initial position (See FIG. 2B and 4B) on tapered portions 44 and 46. This movement of section 52 compresses tubular portion 18 toward tubular portion 20 and closes gap 48. Assembly 12 may then been turned and portions 18 and 20 reexpanded. The angle assembly 12 is turned may be 90 degrees or whatever angle is necessary to seal the rest of the seam.

Once the seam has been completely sealed, portions 18 and 20 on assembly 12 are retracted and then removed from organ 22 through slit 70. It may be preferable that additional optical media be placed in assembly 12 to direct energy to close slit 70 after assembly 12 removal. Depending on the application, the apparatus may contain a mechanism for providing visual feedback for precise positioning in the expansion assembly so that the energy is in alignment with the area being treated.

Preferably one or more optic elements 120–122 are placed adjacent the distal ends of fibers 28a and/or 28b. Optical elements 120 and 122 are connected to fibers 124, respectively, which feed signal from elements 120 and 122 to monitor 128 (FIG. 1). Monitor 128 displays the view of elements 120 and 122. Optic elements 120 and 122 are positioned in assembly 12 to permit the surgeon to view seam 64 of organ 22. The alignment of the optical elements 120 and 122 are selected to ensure that when the surgeon views the seam 64 through optical elements 120 and 122, fibers 28a and 28b deliver welding energy to the seam to weld the organ 22.

Referring to FIGS. 7-11, there is shown an alternate embodiment of assembly 12, and designated as assembly 80. Assembly 80 contain a tubular expansion portion 82 having a first tubular portion 84 and a second tubular portion 86 which engage and disengage with the inner walls of a luminal tissue or organ 22 in response to hand grips (not shown) being depressed and released by the user. Optical energy from energy source (not shown) is fed through conduit 98 using optic media 100a-100b such as a fiber optic cable having proximate and distal ends. The distal end of fiber optic media 100a-100b terminates in assembly 80 and directs optical energy at the inner walls of organ 22.

Expansion portion 82 has a track 88 that guides a distal end of a control portion 90. The distal end of control portion 90 has a hollow and oval shaped gear member 92 with notches 94a-d embedded therein.

Referring to FIGS. 7-11, portions 84 and 86 are shown connected to cylindrical throat portion 102 through cylindrical tapered portions 104 and 106 respectively. Portions 84 and 86 are separated by gap 108 and engage each other with spring 110. A cable or conventional other mechanism (not shown) connects handgrips (not shown) to throat portion 102 and the distal end of control portion 90. The mechanism responds to handgrips (not shown) being engaged to turn gear member 92 in track 88. The expansion of portions 84 and 86 is preferably actuated by a mechanism that provides that the gaps between the portions 84 and 86 expand at predetermined increments.

Figure 10:
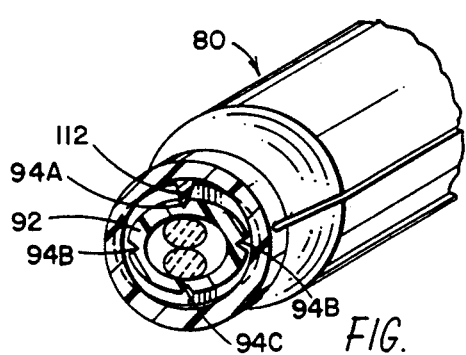
FIG. 10 is a cross sectional view along line 10—10 of FIG. 8.
Figure 11:
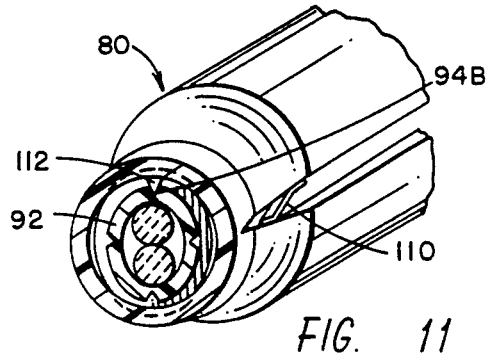
FIG. 11 is cross sectional views along line 11—11 of FIG. 8.

Tapered portion 106 is connected to a tooth 112 that rides along gear member 92. As gear member 92 turns, tooth 112 moves up and down forcing portions 84 and 86 to expand away from and toward each other. Notches 94a-d act as indices to the user to allow precise expansion of the first portion 84 away from portion 86. For example, if the user desires to expand the outside surface of portion 84 1mm away from the outside surface of portion 86, gear member 92 would be turned until the tooth 112 moves from notch 94a to notch 94b. If the user desires to expand the portions 84 and 86 2mm away, tooth 112 would be moved to notch 94c (FIG. 11). If portions 84 and 86 were to be retracted to its initial retracted position, gear member 92 would be turned until tooth 112 resides in notch 94a (FIG. 10).

This concludes the description of the preferred embodiments. A reading by those skilled in the art will bring to mind various changes without departing from the spirit and scope of the invention. It is intended, however, that the invention only be limited by the following appended claims.

What is claimed is:

1. An apparatus for sealing tubular organs, the apparatus comprising:
   a rigid main portion coupled to a rigid tubular portion;
   said main portion and tubular portion having an inner surface and a generally arcuate shaped outer surface;
   means for expanding the tubular portion radially to engage the lumen;
   a source of energy sufficient to heat tissue to form a denatured proteinaceous substance; and
   means for delivering the energy from the source to the inner surface of the tubular portion;
   and means for directing the energy through the inner surface and out the outer surface, when the tubular portion expands to engage the organ, to heat the organ to a temperature within a nondestructive range bounded by a minimum temperature at which tissue forms a denatured proteinaceous substance and a maximum temperature at which water in the tissue would boil.

2. The apparatus as recited in claim 1 wherein said source of energy is optical energy, and wherein said delivering means includes at least one fiber optic cable that has a proximate end connected to said energy source and a distal end attached adjacent said inner surface of said tubular portion such that said cable distal end, moves when said tubular portion expands to maintain a fixed predetermined distance between said distal end and said organ.

3. The apparatus as recited in claim 1 wherein said source of energy is optical energy, and wherein said delivering means includes a plurality of fiber optic cables that has a proximate end connected to said energy source and a distal end engaging with the inner surface of said tubular portion, said distal ends being positioned in a circle around the inner surface of said tubular portion.

4. The apparatus as recited in claim 3 further comprising means for selectively feeding, energy from the source to each of the fiber optic cables independently.

5. A method for sealing an area of organs having a lumen, the method comprising the steps of:
   inserting an apparatus having a tubular portion and a main portion into the lumen of the organ;
   inserting an apparatus having a tubular portion and a main portion into the lumen of the organ;
   positioning the tubular portion in the lumen adjacent the area on the organ to be sealed;
   moving the tubular portion radially to engage the organ when the tubular portion is positioned adjacent the area to be sealed;
   emitting energy from a source sufficient to heat tissue to form a denatured proteinaceous substance;
   delivering the energy from the source to the tubular portion;
   directing energy delivered to the tubular portion outward through the engaged tubular portion and at the area on the lumen to be sealed;
   maintaining the energy delivered to the tubular portion affixed predetermined distance away from the engaged organ as the tubular potion moves away from the main portion; and
   applying the directed energy with sufficient duration and amplitude to heat the lumen to a temperature within a nondestructive range bounded by a minimum temperature at which tissue forms a denatured proteinaceous substance and a maximum temperature at which water in the tissue would boil.

6. The method as recited in claim 5 further comprising the steps of:
   retracting the tubular portion toward the main portion after the directed energy has been applied to the lumen; and
   removing the apparatus from the lumen after retracting the tubular portion.

7. The method as receited in claim 5 further comprising the steps of:

constructing the tubular portion from a material that is substantially transmissive to the energy emitted from the source;

delivering the energy with at least one optical fiber having a proximal end connected to the source and a distal end engaging with an inner surface of the tubular portion; and directing energy from the distal end outward through the inner surface of the transmissive material and at the area to be sealed.

8. The method as recited in claim 7 further comprising the steps of:

delivering the energy to the organ with a plurality of optical fibers having a proximal end connected to the source and a distal end engaging with an inner surface of the tubular portion; and placing the distal end of the optical fibers preferably circumferentially along the perimeter of an inner surface of the transmissive material to seal the edges along the seam of the organ.

9. The method as recited in claim 5 further comprising the steps of:

tightly approximating edges of two tissues of a transected organ in order to form a seam;

constructing the tubular and main portion from a rigid material;

positioning the tubular portion within the lumen of the transected organ so that the area to be welded aligns with the seam; and moving the rigid tubular portion away from the main portion to apply sufficient pressure to hold the lumen and the edges to be sealed in place while the organ is welded.

10. The method as recited in claim 9 further comprising the steps of:

placing an optical element in contact with either said tubular portion or said main portion;

optically sensing the seam of the organ with the optical element;

displaying a video signal showing inside walls of the organ;

delivering the energy from the source outward through the engaged tubular portion and at the area on the lumen to be sealed with an energy delivery media; and positioning the optical elements on the tubular portion to indicate as the organ is displayed when the seam is aligned with the energy delivery media.

11. A method for sealing an seam of a lumen having inner walls, the method comprising the steps of:

placing an apparatus into the lumen of the organ;

placing an optical element in said apparatus that provides a video signal corresponding to images of the inner walls of the lumen;

transferring said video signals to a monitor;

displaying said video signal on said monitor;

moving the apparatus in the lumen until the seam appears on the monitor;

emitting energy from a source sufficient to heat tissue to form a denatured proteinaceous substance when the seam appears on the monitor;

delivering the energy from the source to the apparatus in the lumen and onto the inner walls of the lumen so that the wall may be sealed;

radially aligning on the apparatus the optical element with the location on the inner walls of the lumen where energy is delivered; and applying the delivered energy with sufficient duration and amplitude to heat the lumen to a temperature within a nondestructive range bounded by a minimum temperature at which tissue forms a denatured proteinaceous substance and a maximum temperature at which water in the tissue would boil

* * * * *